(12) United States Patent
O'Yang et al.

(10) Patent No.: US 7,799,816 B2
(45) Date of Patent: Sep. 21, 2010

(54) IMIDAZOLINYLMETHYL ARYL SULFONAMIDE

(75) Inventors: Counde O'Yang, Sunnyvale, CA (US); Robert Greenhouse, Newark, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 12/365,247

(22) Filed: Feb. 4, 2009

(65) Prior Publication Data

US 2009/0197931 A1   Aug. 6, 2009

Related U.S. Application Data

(60) Provisional application No. 61/025,872, filed on Feb. 4, 2008.

(51) Int. Cl.
*A61K 31/4164* (2006.01)
*A61P 13/00* (2006.01)
*C07D 233/06* (2006.01)

(52) U.S. Cl. .................................. 514/401; 548/355.1

(58) Field of Classification Search .............. 548/355.1; 514/401
See application file for complete search history.

(56) References Cited

U.S. PATENT DOCUMENTS

2004/0214875 A1   10/2004   Dillon et al.

FOREIGN PATENT DOCUMENTS

WO   03091236 A1   11/2003

*Primary Examiner*—Kamal A Saeed
(74) *Attorney, Agent, or Firm*—Robert C. Hall (57) ABSTRACT

This invention relates to an alpha-1 A receptor partial agonist, which is represented by Formula I:

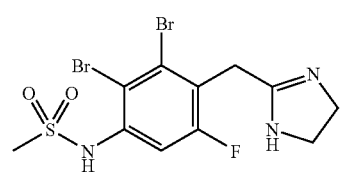

and pharmaceutically acceptable salts or solvates thereof. The invention further relates to pharmaceutical compositions containing formula I, methods for their use as therapeutic agents, and methods of preparation thereof.

11 Claims, 3 Drawing Sheets

Figure 1a. Effect of vehicle on IUP, MAP and HR in Conscious Pig Model

Figure 1b. Formula I in Conscious Pig Model

Figure 1c. Analogue Compound in Conscious Pig Model

IMIDAZOLINYLMETHYL ARYL SULFONAMIDE

CROSS-REFERENCE TO RELATED APPLICATIONS

This application is entitled to the benefit of U.S. provisional patent application Ser. No. 61/025,872 filed on Feb. 4, 2008, the disclosure of which is incorporated herein by reference.

FIELD OF THE INVENTION

This invention relates to an imidazolinylmethyl aryl sulfonamide which is an alpha-1A adrenergic partial agonist, associated pharmaceutical compositions, and methods for use as a therapeutic agent.

BACKGROUND OF THE INVENTION

Alpha-1 adrenergic receptors (interchangeably named alpha-1 adrenoceptors) are G-protein coupled transmembrane receptors that mediate various actions of the sympathetic nervous system through the binding of the catecholamines, epinephrine and norepinephrine (NE). Currently, several subtypes of the alpha-1 adrenergic receptors are known to exist for which the genes have been cloned: alpha-1A (previously known as alpha-1C), alpha-1B and alpha-1D. The existence of a low affinity alpha-1 adrenoceptor for prazosin named alpha-1L, in human prostate has been determined. However, the gene for the alpha-1L adrenergic receptor subtype has yet to be cloned.

The alpha-1 adrenoceptor plays a part in the sympathetic maintenance of smooth muscle tone and alpha-1 adrenergic agonists are known to increase muscle tone in the lower urinary tract necessary for urine storage and urine emptying thus making adrenergic receptors important targets for drug development in urinary dysfunction (Testa, R., *Eur. J. Pharmacol.*, 1993, 249, 307-315. Pharmacological studies resulting in the subdivision of alpha-1 adrenergic receptors have let to the suggestion that development of subtype-selective compounds may allow improved treatment with a lower incidence of side effects, and Tanaguchi et al., *Eur. J. Pharmacol*, 1996, 318, 117-122, have reported that compounds with selectivity for the alpha-1A receptor and to a lessen extent to the alpha-1L receptor over the alpha-1B and alpha-1D subtypes have selectivity for urethral over vascular tissue.

Urinary incontinence is a condition defined as the involuntary loss of urine to such an extent as to become a hygienic or social concern to the patient. Stress urinary incontinence (SUI) occurs when the internal sphincter does not close completely. The primary symptom is minor leakage from activities, such as coughing, sneezing, laughing, running, lifting, or even standing, that apply pressure to a full bladder. Leakage stops when the activity stops. SUI is most common in women between the ages of 25 and 50, and many regularly exercising women have some degree of SUI.

The methods presently available to treat SUI include physiotherapy and surgery. Treatment with pharmaceuticals is limited to the use of non-selective adrenergic agonists. Only a limited number of pharmaceutical agents have been employed, with varying success, to treat stress incontinence.

Phenylpropanolamine, pseudoephrine and midodrine are considered first-line therapy for mild to moderate stress incontinence (Wein, supra; Lundberg (editor), *JAMA* 1989, 261(18):2685-2690). These agents are believed to work both by direct activation of alpha-1 adrenoceptors and indirectly by displacement of endogenous norepinephrine from sympathetic neurons following uptake into the nerve terminal (Andersson and Sjogren, *Progress in Neurobiology*, 1982, 71-89). Activation of alpha-1 adrenoceptors located on the smooth muscle cells of the proximal urethra and bladder neck (Sourander, *Gerontology* 1990, 36:19-26; Wein, supra) evokes contraction and an increase in urethral closure pressure.

The utility of phenylpropanolamine, pseudoephrine, and midodrine is limited by a lack of selectivity among the alpha-1 adrenoceptor subtypes and by the indirect action of these agents (i.e. activation of alpha-1, alpha-2, and beta-adrenoceptors in the central nervous system and periphery). As a result, any desired therapeutic effect of these agents may be accompanied by undesirable side effects such as an increase in blood pressure. The increase in blood pressure is dose-dependent and therefore limits the ability to achieve therapeutically effective circulating concentrations of these agents (Andersson and Sjogren, supra). Furthermore, in some patients these agents produce insomnia, anxiety and dizziness as a result of their central nervous system stimulant actions (Andersson and Sjogren, supra, Wein, supra).

Certain alpha-1A/1L, agonists are known to be useful in treating various disease states including urinary incontinence, nasal congestion, sexual dysfunction such as ejaculation disorders and priapism, and CNS disorders such as depression, anxiety, dementia, senility, Alzheimer's, deficiencies in attentiveness and cognition, and eating disorders such as obesity, bulimia, and anorexia. See for example U.S. Pat. Nos. 5,952,362, 6,756,395, 6,852,726, and 6,979,696 which disclose a variety of 2-imidazolinylmethyl aryl and heteroaryl derivatives as alpha-1A/L agonists. Full agonists of the alpha 1A/1L adrenoceptor subtype, while potentially effective at treating urinary incontinence, can be limited by undesirable cardiovascular and central nervous system side effects. Selective alpha 1A/1L receptor modulators with reduced intrinsic efficacy (i.e., "partial agonists") can reduce such side effects while maintaining the contractile effects on urethral smooth muscle needed for treating incontinence.

Due to side effects and/or limited efficacy associated with the current available medicaments, there is an unmet medical need for useful compounds. A compound having the desired alpha-1A adrenergic partial agonist profile is desirable.

SUMMARY OF THE INVENTION

In one aspect, the application provides a compound of formula I:

or a pharmaceutically acceptable salt or prodrug thereof.

The compound of Formula I, N-[2,3-Dibromo-4-(4,5-dihydro-1H-imidazol-2-ylmethyl)-5-fluoro-phenyl]-methanesulfonamide (nomenclature used in this Application is based on AUTONOM™ v.4.0), has been found to exhibit unexpectedly enhanced selectivity, for enhancement of intraurethral pressure (IUP) over blood pressure (MAP), as a partial agonist of alpha-1A adrenoceptors. The combination of the dibromo substituents on the 2- and 3-positions with the fluoro substituent at the 5-position of the phenyl ring provide unexpected advantages over the general class of imidazolinylmethyl aryl sulfonamides in that it has both a favorable intrinsic activity, or efficacy, as a partial agonist, which is ideally between 0.35 to 0.60, of 0.38 and an affinity, or pEC50 value, of 6.7. As full agonist activity is undesirable due to hypertension related side effects, the combination of high affinity and partial agonist behavior is critical for optimization of urethral activity benefits associated with effective modulation of alpha-1A adrenoceptors coupled with minimization of diastolic blood pressure related side effects. Furthermore, the compound of Formula I, in comparison to analogue compounds, exhibits improved durability of IUP response over time which is necessary for effective treatment of incontinence.

In one embodiment, the application provides the compound of formula I, wherein the pharmaceutically acceptable salt is hydrochloride.

In one embodiment, the application provides a composition comprising the compound of formula 1 and further comprising a pharmaceutically acceptable carrier.

In one embodiment, the application provides the above composition, wherein the composition is suitable for administration to a subject having a disease state which is alleviated by treatment with an alpha-1A receptor partial agonist.

In one embodiment, the application provides a method for preventing, alleviating, or treating a disorder modulated by alpha-1A adrenoceptors, said method comprising administering to a subject in need thereof an effective amount of the compound of formula 1.

In one embodiment, the application provides the above method, wherein the disorder is selected from urge incontinence, stress incontinence, overflow incontinence, and functional incontinence.

In one embodiment, the application provides a method for preventing, alleviating, or treating a disorder modulated by alpha-1A adrenoceptors, wherein the disorder is stress incontinence.

In one embodiment, the application provides a method for preventing, alleviating, or treating a disorder modulated by alpha-1A adrenoceptors, wherein the disorder is urge incontinence.

In one embodiment, the application provides a method for preventing, alleviating, or treating a disorder modulated by alpha-1A adrenoceptors, wherein the disorder is overflow incontinence.

In one embodiment, the application provides a method for preventing, alleviating, or treating a disorder modulated by alpha-1A adrenoceptors, wherein the disorder is functional incontinence.

In one embodiment, the application provides a method for preventing, alleviating, or treating a disorder modulated by alpha-1A adrenoceptors, said method comprising administering to a subject in need thereof an effective amount of the compound of formula 1 in combination with a second modulator of alpha-1A adrenoceptors.

In one embodiment, the application provides a method of treating or preventing a disease state characterized by urinary incontinence comprising administering to a subject in need thereof an effective amount of a compound of formula 1.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

All patents and publications identified herein are incorporated herein by reference in their entirety.

As used herein, "IUP" means intraurethral pressure and is measured as the 2 minute mean from the first peak of the urethral response.

As used herein, "MAP" means mean arterial blood pressure and is measured as the average blood pressure during the 2 minute section where IUP is measured.

As used herein, "durability of IUP response over time" means the slope of the IUP response in mmHg/min and is calculated immediately after the 2 minute IUP response for 5 minutes (2-7 minutes post the first peak) for the top 3 doses.

"Aryl" means the monovalent cyclic aromatic hydrocarbon radical consisting of one or more fused rings in which at least one ring is aromatic in nature, which can optionally be substituted with hydroxy, cyano, lower alkyl, lower alkoxy, alkylthio, halo, haloalkyl, hydroxyalkyl, nitro, alkoxycarbonyl, amino, alkylamino, dialkylamino, aminocarbonyl, carbonylamino, aminosulfonyl, sulfonylamino, nitro, and/or alkylsulphonyl, unless otherwise indicated. Examples of aryl radicals include, but are not limited to, phenyl, naphthyl, biphenyl, indanyl, anthraquinolyl, and the like.

"Arylsulfonyl" means a radical —S(O)₂R where R is an aryl group as defined herein.

"2-Imidazolinylmethyl", "imidazolin-2-ylmethyl", "imidazolinylmethyl", and 4,5-dihydro-1H-imidazol-2-ylmethyl", which may be used interchangeably, mean the moiety designated by the structure:

It is to be understood that the double bond in 2-imidazoline and 2-imidazolinylmethyl may assume other resonance forms. The terms 2-imidazoline 2-imidazolinylmethyl include all such resonance forms.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral compound" means a compound with one or more chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When chiral centers are present, the stereoisomers may be characterized by the absolute configuration (R or S) of the chiral centers. Absolute configuration refers to the arrangement in space of the substituents attached to a chiral center. The substituents attached to a chiral center under consideration are ranked in accordance with the *Sequence Rule* of Cahn, Ingold and Prelog. (Cahn et al. *Angew. Chem. Inter.,* 1966, Edit., 5, 385; errata 511; Cahn et al. *Angew. Chem.,* 1966, 78, 413; Cahn and Ingold, *J. Chem. Soc.* (London), 1951, 612; Cahn et al., *Experientia,* 1956, 12, 81; Cahn, J., *Chem. Educ.,* 1964, 41, 116).

"Tautomers" refers to compounds whose structures differ markedly in arrangement of atoms, but which exist in easy and rapid equilibrium. It should also be understood that when compounds have tautomeric forms, all tautomeric forms are intended to be within the scope of the invention, and the naming of the compounds does not exclude any tautomer form.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state;

(2) inhibiting the disease state, i.e., arresting the development of the disease state or its clinical symptoms; or (3) relieving the disease state, i.e., causing temporary or permanent regression of the disease state or its clinical symptoms.

"$\alpha_1$-adrenergic receptors", "$\alpha_{1A}$-adrenergic receptors" (previously known as "$\alpha_{1C}$-adrenergic receptors"), "$\alpha_{1L}$-adrenergic receptors", or "$\alpha_{1A}/_{1L}$-adrenergic receptors", which may be used interchangeably with "$\alpha_1$-adrenoceptors", "$\alpha_{1A}$-adrenoceptors" (previously known as "$\alpha_{1C}$-adrenoceptors receptors"), "$\alpha_{1L}$-adrenoceptors" or "$\alpha_{1A}/_{1L}$-adrenoceptors" respectively, refers to a molecule conforming to the seven membrane-spanning G-protein receptors, which under physiologic conditions mediate various actions, for example, in the central and/or peripheral sympathetic nervous system through the binding of the catecholamines, epinephrine and norepinephrine.

"Agonist" or "full agonist" means a molecule, such as a compound, a drug, an enzyme activator, or a hormone, that enhances the activity of another molecule or receptor site.

"Partial agonist" means activates a receptor, but only produces a partial physiological response compared to a full agonist.

"Urinary Incontinence" is a condition characterized by the involuntary loss of urine, which is objectively demonstrable. It is both a social and hygienic problem. Stated simply, incontinence results from the failure of the bladder and/or the urethra to work properly, or when the coordination of their functions is defective. It is estimated that at least ten million Americans suffer from incontinence. While the prevalence of incontinence is two-fold higher in females, with the greatest incidence in postmenopausal women, it also affects males.

Urinary incontinence can be classified into four basic types: urge, stress, overflow and functional, and as used herein the term "urinary incontinence" encompasses all four types.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Genuine stress incontinence (outlet incompetence) is the involuntary loss of urine occurring when increases in intra-abdominal pressure cause a rise in intravesical pressure which exceeds the resistance offered by urethral closure mechanisms. Stress incontinent episodes can result from normal activities such as laughing, coughing, sneezing, exercise, or, in severe stress incontinent patients, standing or walking. Physiologically, stress incontinence is often characterized by a descensus of the bladder neck and funneling of the bladder outlet. This type of incontinence is most common in multi-parous women, as pregnancy and vaginal delivery can cause loss of the vesicourethral angle and damage to the external sphincter. Hormonal changes associated with menopause may exacerbate this condition.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

"A method of treating or preventing incontinence" refers to the prevention of or relief from the symptoms of incontinence including involuntary voiding of feces or urine, and dribbling or leakage of feces or urine which may be due to one or more causes including, but not limited to, pathology altering sphincter control, loss of cognitive function, overdistention of the bladder, hyper-reflexia and/or involuntary urethral relaxation, weakness of the muscles associated with the bladder, or neurologic abnormalities.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.4. Any open valency appearing on a carbon, oxygen, sulfur or nitrogen atom in the structures herein indicates the presence of a hydrogen atom. Whenever a chiral carbon is present in a chemical structure, it is intended that all stereoisomers associated with that chiral carbon are encompassed by the structure. Whenever a chemical structure shown herein can exist in a different tautomeric form, it is intended that the structure encompasses such different tautomeric forms.

EXAMPLES

The following preparations and examples are given to enable those skilled in the art to more clearly understand and to practice the present invention. They should not be considered as limiting the scope of the invention, but merely as being illustrative and representative thereof.

General Synthetic Reaction Schemes

The compound of the present invention may be made by the methods depicted in the illustrative synthetic reaction schemes shown and described below.

The starting materials and reagents used in preparing Formula I generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and *Organic Reactions,* Wiley & Soils: New York, 1991, Volumes 1-40. Where necessary, conventional protecting group techniques were used as described by Greene et al., *Protecting Groups in Organic Synthesis,* 3rd Ed., Wiley Interscience, 1999. The following synthetic reaction schemes are merely illustrative of some methods by which the compound of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Chemical Syntheses

Synthetic Scheme

-continued

A. Preparation of
2,3-Dibromo-4,5-difluoro-1-nitro-benzene (1)

1,2-Difluoro-4-nitro-benzene (16 g) was dissolved in sulfuric acid (100 mL,). To this solution was added 1,3-dibromo-5,5-dimethyl-imidazolidine-2,4-dione (30.2 g). As the reaction mixture began to warm, it was cooled in ice and wrapped in aluminum foil. Stirring was continued overnight. The reaction mixture was poured onto a mixture of ice and ethyl acetate and the layers were separated. The water layer was extracted once with ethyl acetate and the combined organic extracts were washed with sodium bisulfite solution, dried, and solvent removed in vacuo. The resulting orange semisolid (33.61 g) was filtered through a thick plug of silica gel in dichloromethane to remove a large amount of colored impurity. The resulting light yellow oil (32.6 g) ran as a single spot on tlc (1:9 ethyl acetate-hexane) but nmr analysis revealed it to be a mixture of the title compound mixed with other components. No further purification was carried out at this point.

B. Preparation of (2,3-Dibromo-6-fluoro-4-nitro-phenyl)-acetonitrile (2)

32 g of a mixture containing 2,3-dibromo-4,5-difluoro-1-nitro-benzene was dissolved in acetonitrile (500 mL) and t-butyl cyanoacetate (19 g) was added. Sodium hydroxide (15.6 g in small pearls) was added and the mixture was vigorously stirred overnight. The solvent was removed in vacuo and the residue was partitioned between ethyl acetate and dilute hydrochloric acid. The layers were separated and the organic layer was washed with saturated sodium chloride solution. The solution was dried and solvent removed in vacuo to afford 51 g of an oil. The crude material was partially purified on a silica gel column to remove more polar material. The major less polar component was heated in vacuo with stirring at 150° C. for about an hour after which time, the bubbling had stopped. The crude material was purified by chromatography on silica gel (hexane-ethyl acetate) to afford 24 g of an oil which contained the title compound as a major component. No further purification was attempted at this point.

C. Preparation of (4-Amino-2,3-dibromo-6-fluoro-phenyl)-acetonitrile (3)

Twenty-four grams of a mixture containing (2,3-dibromo-6-fluoro-4-nitro-phenyl)-acetonitrile was dissolved in ethanol (500 mL) and tin (II) chloride dihydrate (85 g) was added. The mixture was stirred and heated at 75° C. for 5 h. 10 g more tin chloride was added and the mixture was heated at reflux for 30 additional minutes. The solution was cooled and most of the ethanol was removed in vacuo. The reaction mixture was diluted to a volume of 600 mL with ethyl acetate and 100 mL water was added. With stirring, sodium bicarbonate (75 g) was slowly added. The ethyl acetate layer was separated and the aqueous layer extracted a second time with ethyl acetate. The combined organic extracts were dried and the solvent removed in vacuo to afford 22.8 g of crude product. The title compound (3.8 g) was obtained from the crude mixture by column chromatography (hexane-ethyl acetate; then hexane-methylene chloride mixtures).

D. Preparation of (4-(bis-methylsulfonyl)amino-2,3-dibromo-6-fluoro-phenyl)-acetonitrile (4)

(4-Amino-2,3-dibromo-6-fluoro-phenyl)-acetonitrile (3.61 g) was dissolved in dichloromethane (125 ml) and triethyl amine (5.0 mL) was added. The solution was cooled in ice and a solution of methanesulfonyl chloride (2.30 mL) in dichloromethane (25 mL) was added dropwise with stirring under nitrogen. The ice bath was removed and the reaction mixture was allowed to reach room temperature and stirred overnight. The reaction mixture was diluted with water and the organic layer separated, dried and evaporated to dryness. The crude residue was purified by column chromatography. Elution with ethyl acetate-hexane mixtures afforded 2.7 g of the title compound.

E. Preparation of N-[2,3-Dibromo-4-(4,5-dihydro-1H-imidazol-2-ylmethyl)-5-fluoro-phenyl]-methanesulfonamide hydrochloride (hydrochloride salt of Formula I)

(4-(bis-methylsulfonyl)amino-2,3-dibromo-6-fluoro-phenyl)-acetonitrile (1.91 g) was dissolved in anhydrous ethylene diamine (20 mL). Following the initial exotherm, 1 drop of carbon disulfide was added. The clear solution was flushed with argon and sealed with a Teflon-lined cap. The reaction vessel was placed in an oil bath preheated to 130° C. and stirred at that temperature for 2 h. The crude reaction mixture was concentrated and purified on silica gel, eluting first with ethyl acetate followed by a mixture of dichloromethane-methanol-ammonium hydroxide. Further purification by preparative tlc afforded the pure free base which was converted to its hydrochloride salt (0.276 g) by treatment with HCl in ether (MP 182.3-183.5; MS [M+H]+ 428/430/432).

General Utility

The compound of the present invention have selective alpha-1A adrenergic selective activity and as such are expected to be useful in the treatment of various disease states, such as urinary incontinence; nasal congestion; sexual dysfunction, such as ejaculation disorders and priapism; CNS disorders such as depression, anxiety, dementia, senility, Alzheimer's, deficiencies in attentiveness and cognition, and eating disorders such as obesity, bulimia, and anorexia.

Urinary incontinence (UI) is a condition defined as the involuntary loss of urine to such an extent as to become a hygienic or social concern to the patient. Involuntary loss of urine occurs when pressure inside the bladder exceeds retentive pressure of the urethral sphincters (intraurethral pressure). Four major types of urinary incontinence have been defined based on symptoms, signs and condition: stress, urge, overflow and functional incontinence.

Stress urinary incontinence (SUI) is the involuntary loss of urine during coughing, sneezing, laughing, or other physical activities. The present methods to treat SUI include physiotherapy and surgery. Treatment with pharmaceutical agents is limited to the use of non selective-adrenergic agonists like phenylproanolamine and midodrine. The rationale for the use of adrenergic agonists for the treatment of SUI is based on physiological data indicating an abundant noradrenergic input to smooth muscle of the urethra.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

The compound of this invention are also particularly useful for the treatment of nasal congestion associated with allergies, colds, and other nasal disorders, as well as the sequelae of congestion of the mucous membranes (for example, sinusitis and otitis media). with less or no undesired side effects.

These and other therapeutic uses are described, for example, in *Goodman & Gilman's, The Pharmacological Basis of Therapeutics*, ninth edition, McGraw-Hill, New York, 1996, Chapter 26:601-616; and Coleman, R. A., *Pharmacological Reviews*, 1994, 46:205-229.1

Testing

Figure 1A:
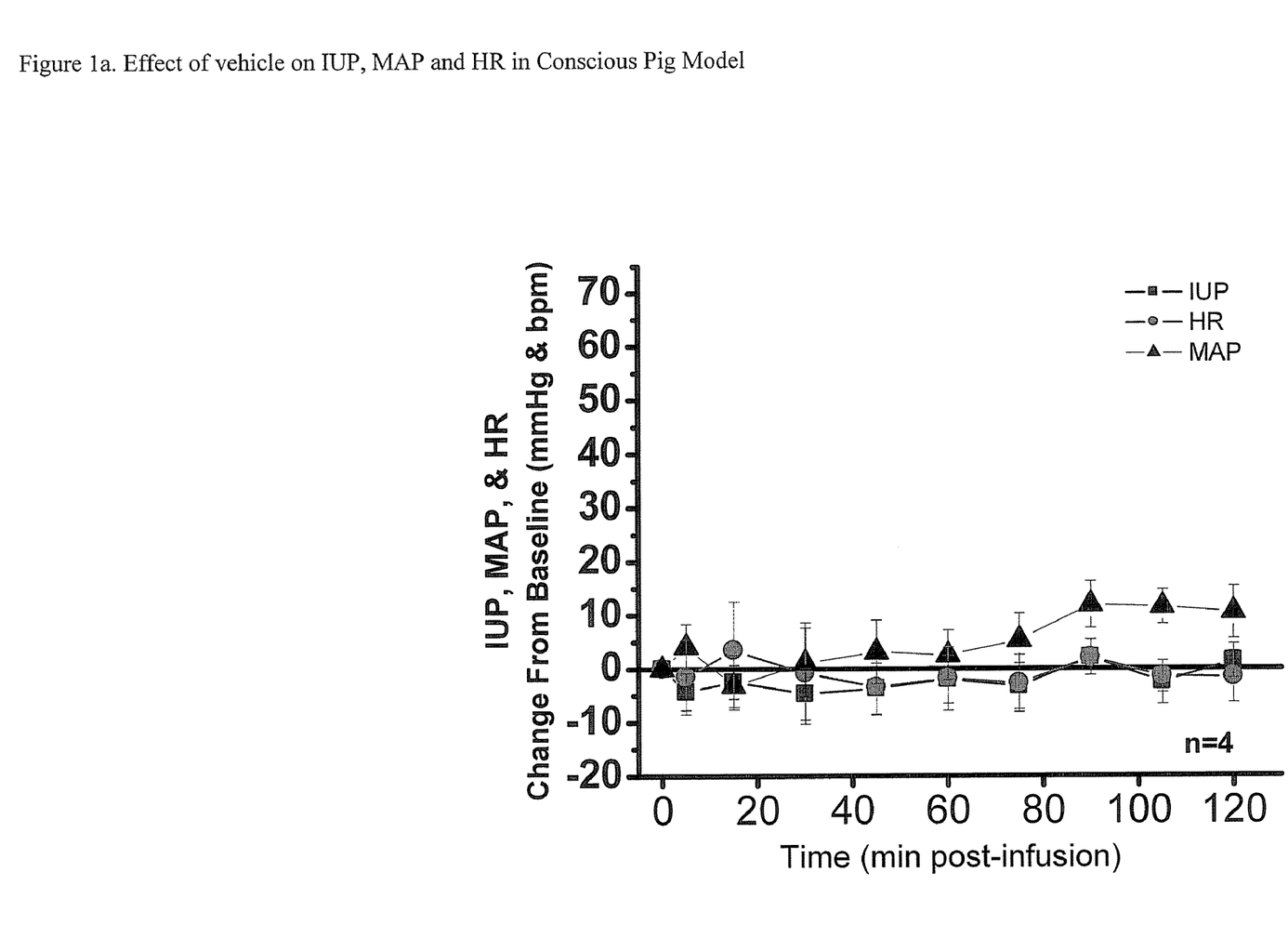
FIG. 1a. Effect of vehicle on IUP, MAP and HR in Conscious Pig Model
FIG. 1b. Formula I in Conscious Pig Model
FIG. 1c. Analogue Compound in Conscious Pig Model
Figure 1B:
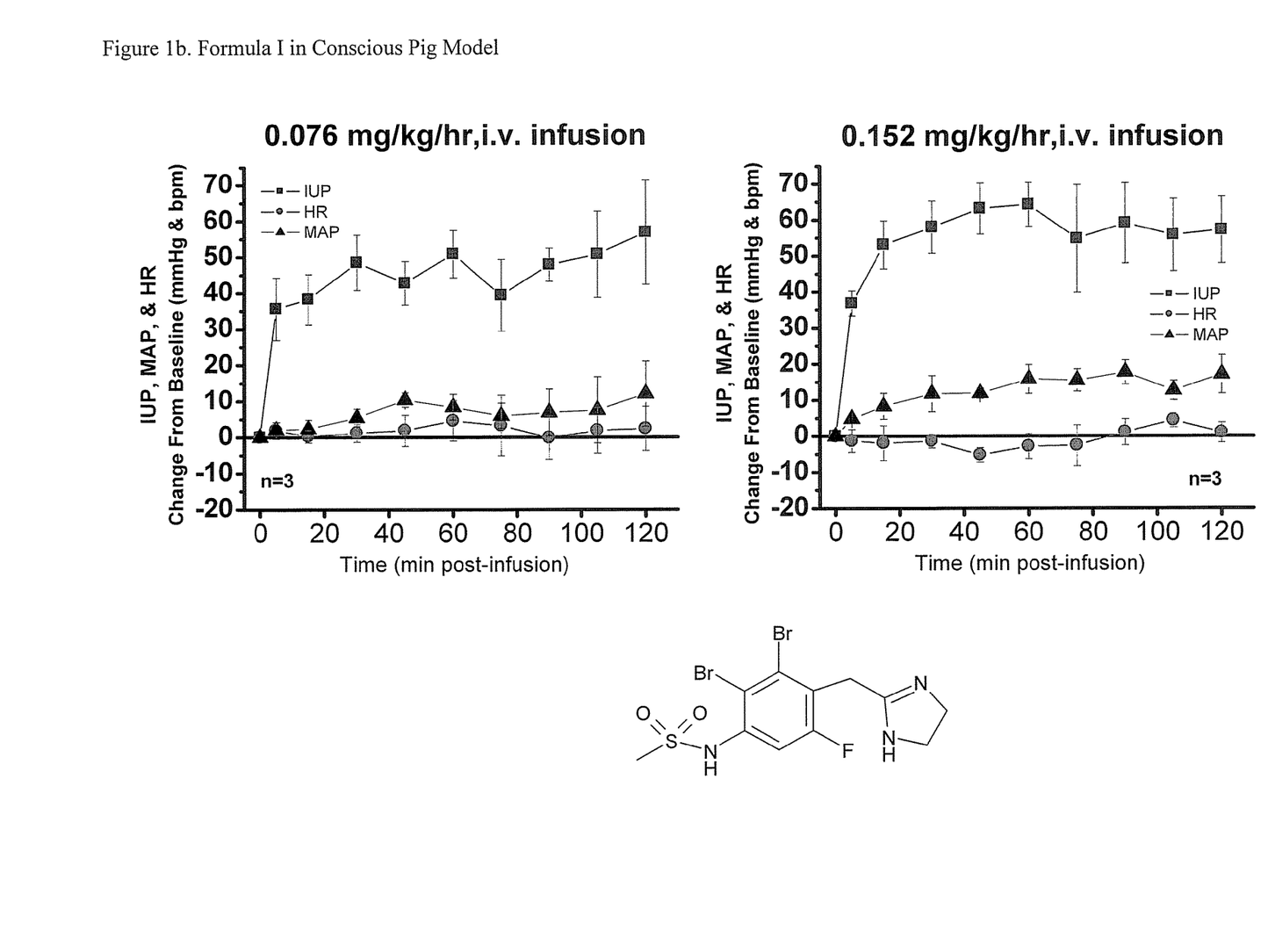
Figure 1C:
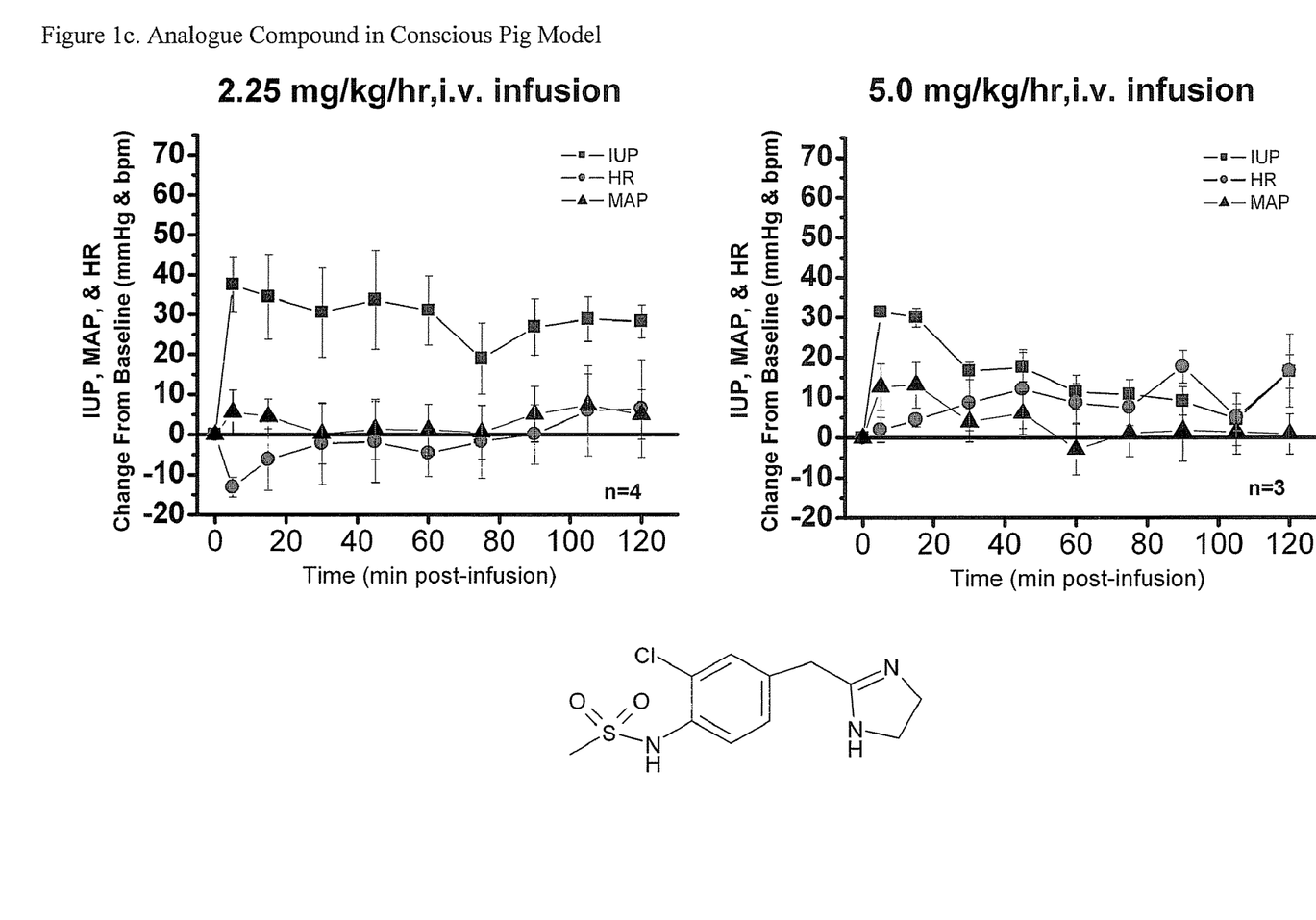

General Strategy for Testing Alpha-1A Adrenoceptor Partial Agonists:

In general, IUP is the intraurethral pressure and is measured as the 2 minute mean from the first peak of the urethral response (FIG. 1). MAP is the mean arterial blood pressure and is measured as the average blood pressure during the 2 minute section where IUP is measured. The durability is the slope of the IUP response in mmHg/min and is calculated immediately after the 2 minute IUP response for 5 minutes (2-7 minutes post the first peak) for the top 3 doses.

Conscious Pig Materials and Methods

Sling Training: Female Yucatan Micro-Swine were trained to stay in a sling for up to 4 hours. Swine were exposed to progressively longer sling durations per IACUC sling-training guideline. Swine were chosen for surgical instrumentation only if they exhibited acceptable tolerance for sling exposure.

Surgical Instrumentation: Female Yucatan Micro-swine were instrumented with a telemetry device with both pressure and ECG monitoring capabilities (Data Sciences International St Paul Minn.). In addition, a Bardport low profile titanium VAP was placed subcutaneously for blood sampling. All devices were implanted by the surgical veterinarian at Roche Palo Alto. Briefly, the telemetry probe body was placed subcutaneously in the cervical region. The intra-arterial pressure catheter was advanced via the superficial cervical artery into the subclavian artery for blood pressure measurement. The ECG leads were placed intra-muscularly: one in the intercostal muscle between the T8-T10 regions on the left side, and the other in the intercostal muscles between the T1-T3 regions on the right side. The VAP was placed subcutaneously in the neck region, with the catheter advanced into the jugular vein. Swine were allowed to fully recover from the surgery (typically 10 days).

Pre-Experiment: On the day of the study, the swine were anesthetized to effect with Isoflurane/O2 in the animal colony. A catheter was placed into an ear vein and the swine sedated with approximately 2 mg/kg, po bolus of propofol as isoflurane/O2 was discontinued. The swine was then transported to the study room and placed on intravenous propofol infusion (~12 mg/kg/hr, iv). The vulva and surrounding area were aseptically prepared and a sterile 8-Fr 4-sensor solid state pressure transducer (Unisensor, Roterdam, Switzerland) was inserted through the external urethral meatus into the bladder. Placement of the catheter was confirmed via urethral profilometry (the third most distal transducer was placed at the high pressure zone of the urethra). The catheter was anchored into place by sutures placed in the skin surrounding the vulva and attached to tape fixed to the catheter. After aseptic preparation of the VAP site a huber needle with tubing assembly was placed in the VAP for serial blood sampling. Propofol infusion was ceased and the swine was allowed to wake up.

Experiment: After the swine was fully awake and stable (usually approximately 1 hour post wake up), baseline blood pressure, IUP, and heart rate parameters were determined. Formula I or vehicle (0.9% saline) was infused via the ear vein at 1 ml/min via an infusion pump for two hours. Blood samples were taken at 5, 15, 30, 45, 60, 75, 90, 105, and 120 minutes post infusion initialization (FIG. 2a). The pig was offered food and water during the experiment.

Data Generating and Analysis Systems: Cardiovascular readings were generated by the TL11M3-D70-PCP (Data Sciences International, St. Paul, Minn.) telemetry device and associated hardware. The device, when activated, transmits its signal to a receiver which forwards this signal to the data exchange matrix. The data exchange matrix then sends its signal stream to the Data-Quest ART Gold version 4.0 which processes and generates cardiovascular data. IUP was monitored by a solid state catheter connected to a TA6000 Polygraph (Data Sciences International, St. Paul, Minn.). An analogue signal from the TA6000 was sent to either a Gould Acquisition Interface or Power Lab data acquisition system and this data was processed by either the Ponema software version 3.2 (Data Sciences International, St. Paul, Minn.) or Power Lab Chart version 5.0.2 (ADInstruments, Colorado Springs, Colo.).

Measurements: Baseline included a two-minute sampling period just prior to infusion for IUP, MAP, and HR. Post-dose time points included two-minute sampling periods at approximately 5, 15, 30, 45, 60, 75, 90, 105, and 120 minutes post-infusion initialization for IUP, MAP, and HR. Typically, post-dose time points were sampled for two minutes leading up to the blood sample (e.g. 58-60 min post dose). If pig activity caused aberrant data points (typically a marked increase in HR) the two minute sampling period was moved either a few minutes before or after active period. Data was considered invalid for a sampling period and not reported if the following was observed: 1) Persistent activity during a specific time point which lead to a sustained increase in HR and/ or 2) swine defecation which led to a substantial change in IUP. Change from baseline was calculated as post-dose value-pre-dose value.

RESULTS

The compound of Formula I has been found to exhibit unexpectedly enhanced selectivity, for enhancement of intraurethral pressure (IUP) over blood pressure (MAP), as a partial agonist of alpha-1A adrenoceptors. The combination of the dibromo substituents on the 2- and 3-positions with the fluoro substituent at the 5-position of the phenyl ring provide unexpected advantages over the general class of imidazolinylmethyl aryl sulfonamides in that it has both a favorable intrinsic activity, or efficacy, as a partial agonist, which is ideally between 0.35 to 0.60, of 0.38 and an affinity, or pEC50 value, of 6.7. As full agonist activity is undesirable due to hypertension related side effects, the combination of high affinity and partial agonist behavior is critical for optimization of urethral activity benefits associated with effective modulation of alpha-1A adrenoceptors coupled with minimization of diastolic blood pressure related side effects. Furthermore, the compound of Formula I, in comparison to analogue compounds, exhibits improved durability of IUP response over time which is necessary for effective treatment of incontinence.

The compound of formula I tested in the conscious pig model exhibited unexpectedly increased durability of IUP response over time (FIG. 1b) compared to an analogue compound, differing from the compound of formula I with the absence of the 3-bromo and 5-flouro substituents and substitution of a 2-chloro for the 2-bromo on the phenyl ring (FIG. 1c). Additionally, the compound of formula I has selectivity for enhancement of intraurethral pressure (IUP) over blood pressure (MAP). The compound of formula I also has a correspondingly low maximum arterial blood pressure effect. These characteristics, in combination, contribute to render the compound of formula I a remarkably superior pharmaceutical candidate over structurally similar analogues, both selectively, for enhancement of intraurethral pressure (IUP) over blood pressure (MAP), and effectively over time, as an alpha-1A partial agonist for the treatment of incontinence.

Administration and Pharmaceutical Composition

The present invention includes pharmaceutical compositions comprising the compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compound of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg, depending upon numerous factors such as the severity of the disease to be treated, the age and relative health of the subject, the potency of the compound, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compound of the present invention for a given disease.

In general, the compound of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

The compound of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compound of the present invention may be formulated in a wide variety of oral administration dosage forms. The pharmaceutical compositions and dosage forms may comprise the compound the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compound of the present invention may be formulated for parenteral administration (e.g., by injection, for example bolus injection or continuous infusion) and may be presented in unit dose form in ampoules, pre-filled syringes, small volume infusion or in multidose containers with an added preservative. The composition may take such form as a suspension, solution, or emulsion in oily or aqueous vehicles, for example a solution in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compound of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compound of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compound of the present invention may be formulated for vaginal administration. Pessaries, tampons, creams, gels, pastes, foams or sprays containing in addition to the active ingredient such carriers as are known in the art to be appropriate.

The compound of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compound of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compound of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone(1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing the compound of the present invention are described in the Examples.

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures, etc.), but some experimental error and deviation should, of course, be allowed for as well as due to differences such as, for example, in calibration, rounding of numbers, and the like.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed:

1. A compound of the formula 1:

or a pharmaceutically acceptable salt thereof.

2. The compound of claim 1, wherein the pharmaceutically acceptable salt is hydrochloride.

3. A composition comprising the compound of claim 1 and further comprising a pharmaceutically acceptable carrier.

4. The composition of claim 3, wherein the composition is suitable for administration to a subject having a disease state which is alleviated by treatment with an alpha-1A receptor partial agonist.

5. A method for preventing, alleviating, or treating a urinary incontinence disorder, said method comprising administering to a subject in need thereof an effective amount of the compound of claim 1.

6. The method of claim 5, wherein the disorder is selected from urge incontinence, stress incontinence, overflow incontinence, and functional incontinence.

7. The method of claim 6, wherein the disorder is stress incontinence.

8. The method of claim 6, wherein the disorder is urge incontinence.

9. The method of claim 6, wherein the disorder is overflow incontinence.

10. The method of claim 6, wherein the disorder is functional Incontinence.

11. A method of treating or preventing a disease state characterized by urinary incontinence comprising administering to a subject in need thereof an effective amount of the compound of claim 1.

* * * * *